United States Patent [19]
Yokoyama et al.

[11] Patent Number: 5,925,664
[45] Date of Patent: *Jul. 20, 1999

[54] METHOD FOR TREATING OCULAR HYPERTENSION AND GLAUCOMA

[75] Inventors: Tomihisa Yokoyama; Tsunemichi Hosokawa; Hiroaki Yanagisawa, all of Tokyo, Japan

[73] Assignee: Sankyo Company, Limited, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/725,197

[22] Filed: Sep. 16, 1996

Related U.S. Application Data

[63] Continuation of application No. PCT/JP95/00444, Mar. 16, 1995, abandoned.

[30] Foreign Application Priority Data

Mar. 16, 1994 [JP] Japan ................................. 6-045404
Mar. 16, 1995 [JP] Japan ................................. 5-000444

[51] Int. Cl.[6] ................................. A61K 31/41
[52] U.S. Cl. ................................. 514/382; 514/913
[58] Field of Search ................................. 514/382, 913

[56] References Cited

U.S. PATENT DOCUMENTS

| | | |
|---|---|---|
| 4,820,843 | 4/1989 | Aldrich et al. . |
| 5,126,342 | 6/1992 | Chakravarty et al. . |
| 5,138,069 | 8/1992 | Carini et al. . |
| 5,219,856 | 6/1993 | Olson . |
| 5,310,929 | 5/1994 | Ardecky et al. . |
| 5,328,919 | 7/1994 | Naka et al. . |
| 5,616,599 | 4/1997 | Yanagisawa et al. . |
| 5,646,171 | 7/1997 | Yanagisawa et al. . |

FOREIGN PATENT DOCUMENTS

| | | |
|---|---|---|
| 0 253 310 | 1/1988 | European Pat. Off. . |
| 0 291 969 | 11/1988 | European Pat. Off. . |
| 0 503 785 | 10/1992 | European Pat. Off. . |
| 0 573 218 | 12/1993 | European Pat. Off. . |
| 0 603 001 | 6/1994 | European Pat. Off. . |
| 631 780 | 1/1995 | European Pat. Off. . |
| 89/06233 | 7/1989 | WIPO . |
| 91/00277 | 1/1991 | WIPO . |
| 91/15206 | 10/1991 | WIPO . |
| 95/01176 | 1/1995 | WIPO . |
| 95/21609 | 8/1995 | WIPO . |

OTHER PUBLICATIONS

Mathis et al, "Angiotensin–II Antagonists Reduce Intraocular Pressure By A Combined Effect On Aqueous Humour Synthesis And Outflow", Abstract 1060–6:06 of the Abstracts published Mar. 15, 1994 for the Annual Meeting of "The Association for Research in Vision and Ophthalmology" held in Florida, May 1–6, 1994.

*Primary Examiner*—Zohreh Fay
*Attorney, Agent, or Firm*—Frishauf, Holtz, Goodma, Langer & Chick, P.C.

[57] ABSTRACT

A method of treating ocular hypertension and/or glaucoma in a mammal by locally administering to the eyes of a mammal a composition comprising an effective amount of a compound of the formula (I)

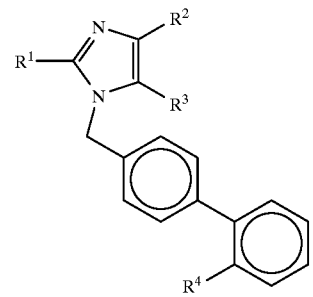

wherein $R^1$ is lower alkyl, lower alkenyl, or $R^5$—A—B—, where $R^5$ is hydrogen, lower alkyl, cycloalkyl or aliphatic acyl; A is oxygen or sulfur; and B is a single bond or a lower alkylene; $R^2$ is lower alkyl, lower alkenyl, or —$C(R^6)(R^7)(R^8)$, wherein $R^6$ is hydroxyl or lower alkoxy; and $R^7$ and $R^8$ each is hydrogen, lower alkyl, lower alkenyl, lower alkynyl, cycloalkyl, aryl or aralkyl; $R^3$ is carboxyl or —$CON(R^9)(R^{10})$, wherein $R^9$ and $R^{10}$ each is hydrogen or lower alkyl; $R^4$ is carboxyl, carboxycarbonyl or tetrazol-5-yl; or a pharmacologically acceptable salt or ester thereof.

64 Claims, No Drawings

METHOD FOR TREATING OCULAR HYPERTENSION AND GLAUCOMA

This application is a continuation application of International Application PCT/JP95/00444 filed Mar. 16, 1995 (now abandoned).

TECHNOLOGICAL FIELD

The present invention relates to an excellent ocular tension lowering agent and/or a glaucoma therapeutic agent for eye drops and/or relates to their uses as an ocular tension lowering agent and/or a glaucoma therapeutic agent for eye drops, and in addition relates to an excellent method of medical treatment administering the agent to mammals with ocular hypertension and/or with glaucoma diseases.

TECHNOLOGICAL BACKGROUND

Hitherto, the use of an angiotensin II inhibitor for the purpose of lowering ocular tension has been described in reports. However, there are a few cases where the effect has been certified in actual experiment, and only oral use of the inhibitor has been described.

On the other hand, if the inhibitor is used only for the purpose of lowering ocular tension, its local application may be preferable because of less adverse reactions and in fact has been desired so far. Only one preceding invention, however, has been disclosed in International Publication WO 91/15206, where angiotensin II inhibitors (in particular, DUP-753 shown by the following formula) can be locally applied by dropping in the eyes for the therapy of ocular hypertension.

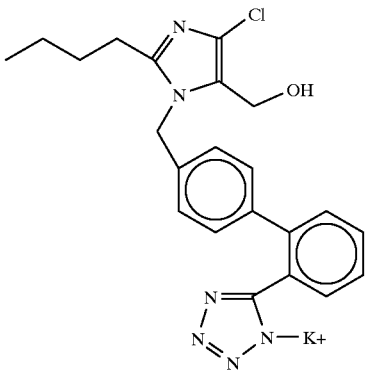

DUP-753

However, in order to use the inhibitor as eye drops, the effect of administering the inhibitor as eye drops in the invention disclosed in the aforesaid International Publication was not enough to use the inhibitor as a medicament.

Though after the Priority Date of the present invention, G. A. Mathis et al. of CIBA Vision Ophtha reported that eye application of angiotensin II inhibitors, CGP 48933 and CGP 49870, showed ocular tension lowering activity, in the annual meeting of "The Association for Research in Vision and Ophthalmology" held in Florida from May 1st to 6th, 1994; and the abstracts including this report were published under date of Mar. 15th, 1994.

PROCESS OF INVENTION

For a long time, the present inventors studied eagerly a novel ocular tension lowering agent and/or a glaucoma therapeutic agent for eye drops and/or their uses as an ocular tension lowering agent and/or a glaucoma therapeutic agent for eye drops, and in addition a method of medical treatment administering the agent to mammals with ocular hypertension and/or glaucoma diseases. Our study resulted in finding that our novel compositions showed an excellent ocular tension lowering and/or a glaucoma therapeutic effect even by its local application such as dropping in the eyes without adverse reactions, and in completion of the present invention.

CONSTITUTION OF INVENTION

The novel ocular tension lowering agent and/or a glaucoma therapeutic agent for eye drops of the present invention comprises an effective amount of compounds having general formula (I):

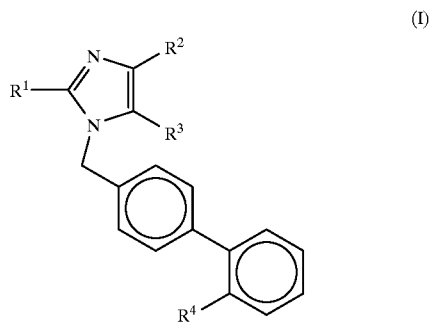

(I)

[wherein $R^1$ represents a lower alkyl group, a lower alkenyl group or a group of formula: $R^5$—A—B— (wherein R represents a hydrogen atom, a lower alkyl group, a cycloalkyl group or an aliphatic acyl group; A represents an oxygen atom or a sulfur atom; and B represents a single bond or a lower alkylene group);

$R^2$ represents a lower alkyl group, a lower alkenyl group or a group of formula: —C($R^6$)($R^7$)($R^8$) (wherein $R^6$ represents a hydroxyl group or a lower alkoxy group; and $R^7$ and $R^8$ are the same or different and each represents a hydrogen atom, a lower alkyl group, a lower alkenyl group, a lower alkynyl group, a cycloalkyl group, an aryl group or an aralkyl group);

$R^3$ represents a carboxyl group or a group of formula: —CON($R^9$)($R^{10}$) [wherein $R^9$ and $R^{10}$ are the same or different and each represents a hydrogen atom, a lower alkyl group or a lower alkyl group substituted by 1 to 3 substituents selected from Substituent group (I)); and $R^4$ represents a carboxyl group, a carboxycarbonyl group or a tetrazol-5-yl group], pharmacologically acceptable salts thereof, or esters or other derivatives thereof;

in the novel use of the invention, the said compounds are used as an ocular tension lowering agent and/or a glaucoma therapeutic agent for eye drops; and, in addition, in the novel medical treatment of ocular hypertension and/or glaucoma diseases in accordance with the invention, an effective amount of the said compounds is administered to mammals.

Among the aforesaid compounds capable of being used as an ocular tension lowering agent and/or a glaucoma therapeutic agent for eye drops, the use of an ocular tension lowering agent and/or a glaucoma therapeutic agent for eye drops, and/or the medical treatment of ocular hypertension and/or glaucoma diseases in accordance with the invention, the preferred compounds are those in which:

(1) $R^1$ represents a group of formula: $R^5$—A—B— (wherein $R^5$ represents a hydrogen atom, a lower alkyl group or an aliphatic acyl group; A represents an oxygen atom or a sulfur atom; and B represents a single bond or a lower alkylene group);

(2) $R^1$ represents a lower alkyl group or a lower alkenyl group;

(3) $R^1$ represents a lower alkyl group;

(4) $R^1$ represents an alkyl group containing 1 to 4 carbon atoms;

(5) $R^1$ represents an alkyl group containing 2 to 4 carbon atoms;

(6) $R^1$ represents a group of formula: —$C(R^6)(R^7)(R^8)$ (wherein $R^6$ represents a hydroxyl group or a lower alkoxy group, and $R^7$ and $R^8$ are the same or different and each represents a hydrogen atom, a lower alkyl group or a lower alkenyl group);

(7) $R^7$ and $R^8$ are the same or different and each represents a hydrogen atom or a lower alkyl group;

(8) $R^6$ represents a hydroxyl group, and $R^7$ and $R^8$ are the same or different and each represents a hydrogen atom or an alkyl group containing 1 to 4 carbon atoms;

(9) $R^7$ and $R^8$ are the same or different and each represents a hydrogen atom or an alkyl group containing 1 or 2 carbon atoms;

(10) $R^2$ represents a 1-hydroxy-1-methylethyl group;

(11) $R^3$ represents a carboxyl group or a group of formula: —$CON(R^9)(R^{10})$ (wherein $R^9$ and $R^{10}$ are the same or different and each represents a hydrogen atom or a lower alkyl group);

(12) $R^3$ represents a carboxyl group;

(13) $R^4$ represents a carboxyl group or a tetrazol-5-yl group;

(14) $R^4$ represents a tetrazol-5-yl group;

(15) $R^1$ represents a lower alkyl group or a lower alkenyl group; $R^2$ represents a group of formula: —$C(R^6)(R^7)(R^8)$ (wherein $R^6$ represents a hydroxyl group or a lower alkoxy group; and $R^7$ and $R^8$ are the same or different and each represents a hydrogen atom or a lower alkyl group); $R^3$ represents a carboxyl group or a group of formula: —$CON(R^9)(R^{10})$ (wherein $R^9$ and $R^{10}$ are the same or different and each represents a hydrogen atom or a lower alkyl group); and $R^4$ represents a carboxyl group or a tetrazol-5-yl group;

(16) $R^1$ represents a lower alkyl group or a lower alkenyl group; $R^2$ represents a group of formula: —$C(R^6)(R^7)(R^8)$ (wherein $R^6$ represents a hydroxyl group or a lower alkoxy group; and $R^7$ and $R^8$ are the same of different and each represents a hydrogen atom or a lower alkyl group); $R^3$ represents a carboxyl group or a group of formula: —$CON(R^9)(R^{10})$ (wherein $R^9$ and $R^{10}$ are the same or different and each represents a hydrogen atom or a lower alkyl group); and $R^4$ represents a tetrazol-5-yl group;

(17) $R^1$ represents a lower alkyl group or a lower alkenyl group; $R^2$ represents a group of formula: —$C(R^6)(R^7)$ $(R^8)$ (wherein $R^6$ represents a hydroxyl group or a lower alkoxy group; and $R^7$ and $R^8$ are the same or different and each represents a hydrogen atom or a lower alkyl group); $R^3$ represents a carboxyl group; and $R^4$ represents a carboxyl group or a tetrazol-5-yl group;

(18) $R^1$ represents a lower alkyl group or a lower alkenyl group; $R^2$ represents a group of formula: —$C(R^6)(R^7)$ $(R^8)$ (wherein $R^6$ represents a hydroxyl group or a lower alkoxy group; and $R^7$ and $R^8$ are the same or different and each represents a hydrogen atom or a lower alkyl group); $R^3$ represents a carboxyl group; and $R^4$ represents a tetrazol-5-yl group;

(19) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group or a group of formula: —$CON(R)(R^{10})$ (wherein $R^9$ and $R^{10}$ are the same or different and each represents a hydrogen atom or a lower alkyl group); and $R^4$ represents a carboxyl group or a tetrazol-5-yl group;

(20) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same of different and each represents a hydrogen atom or an alkyl group containing 1 to 4 carbon atoms); $R^3$ represents a carboxyl group or a group of formula: —$CON(R^9)(R^{10})$ (wherein $R^9$ and $R^{10}$ are the same or different and each represents a hydrogen atom or a lower alkyl group); and $R^4$ represents a tetrazol-5-yl group;

(21) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group; and $R^4$ represents a carboxyl group or a tetrazol-5-yl group;

(22) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group; and $R^4$ represents a tetrazol-5-yl group;

(23) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group or a group of formula: —$CON(R^9)(R^{10})$ (wherein $R^9$ and $R^1$ are the same or different and each represents a hydrogen atom or a lower alkyl group); and $R^4$ represents a carboxyl or tetrazol-5-yl group;

(24) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group or a group of formula: —$CON(R^9)(R^{10})$ (wherein $R^9$ and $R^{10}$ are the same or different and each represents a hydrogen atom or a lower alkyl group); and $R^4$ represents a tetrazol-5-yl group;

(25) $R^1$ represents a lower alkyl group or a lower alkenyl group; $R^2$ represents a group of formula: —$C(R^6)(R^7)$ $(R^8)$ (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group; and $R^4$ represents a carboxyl group or a tetrazol-5-yl group;

(26) $R^1$ represents a lower alkyl group or a lower alkenyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group; and $R^4$ represents a tetrazol-5-yl group;

(27) $R^1$ represents a lower alkyl group; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a carboxyl group or a tetrazol-5-yl group;

(28) $R^1$ represents a lower alkyl group; $R^2$ represents a group of formula: —C($R^9$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a tetrazol-5-yl group;

(29) $R^1$ represents a lower alkyl group; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group; and $R^4$ represents a carboxyl group or a tetrazol-5-yl group;

(30) $R^1$ represents a lower alkyl group; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group; and $R^4$ represents a tetrazol-5-yl group;

(31) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a carboxyl group or a tetrazol-5-yl group;

(32) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a tetrazol-5-yl group;

(33) $R^1$ represents a lower alkyl group; $R^2$ represents a group of formula: —($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group; and $R^4$ represents a carboxyl group or a tetrazol-5-yl group;

(34) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group; and $R^4$ represents a tetrazol-5-yl group;

(35) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a carboxyl group or a tetrazol-5-yl group;

(36) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a tetrazol-5-yl group;

(37) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group; and $R^4$ represents a carboxyl group or a tetrazol-5-yl group;

(38) $R^1$ represents a lower alkyl group; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group; and $R^4$ represents a tetrazol-5-yl group;

(39) $R^1$ represents an alkyl group containing 2 to 4 carbon atoms; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a carboxyl group or a tetrazol-5-yl group;

(40) $R^1$ represents an alkyl group containing 2 to 4 carbon atoms; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a tetrazol-5-yl group;

(41) $R^1$ represents an alkyl group containing 2 to 4 carbon atoms; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group; and $R^4$ represents a carboxyl or tetrazol-5-yl group;

(42) $R^1$ represents an alkyl group containing 2 to 4 carbon atoms; $R^2$ represents a group of formula: —C($R^6$)($R^7$)($R^8$) (wherein $R^6$ represents a hydroxyl group or a lower alkoxy group; and $R^7$ and $R^8$ are the same or different and each represents a hydrogen atom or a lower alkyl group); $R^3$ represents a carboxyl group; and $R^4$ represents a tetrazol-5-yl group;

(43) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a carboxyl group or a tetrazol-5-yl group;

(44) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a tetrazol-5-yl group;

(45) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 to 4 carbon atoms); $R^3$ represents a carboxyl group; and $R^4$ represents a carboxyl group or a tetrazol-5-yl group;

(46) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same of different and each represents a hydrogen atom or an alkyl group containing 1 to 4 carbon atoms); $R^3$ represents a carboxyl group; and $R^4$ represents a tetrazol-5-yl group;

(47) $R^1$ represents an alkyl group containing 2 to 4 carbon atoms: $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a carboxyl group or a tetrazol-5-yl group;

(48) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group or a group of formula: —CON($R^9$)($R^{10}$) (wherein $R^9$ and $R^{10}$ are the same or different and each represents a hydrogen atom or a lower alkyl group); and $R^4$ represents a tetrazol-5-yl group;

(49) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group; and $R^4$ represents a carboxyl group or a tetrazol-5-yl group;

(50) $R^1$ represents an alkyl group containing 2 to 4 carbon atoms; $R^2$ represents a group of formula: —C($R^6$)($R^7$)($R^8$) (wherein $R^6$ represents a hydroxyl group; and $R^7$ and $R^8$ are the same or different and each represents a hydrogen atom or an alkyl group containing 1 or 2 carbon atoms); $R^3$ represents a carboxyl group; and $R^4$ represents a tetrazol-5-yl group;

(51) A compound having the following formula:

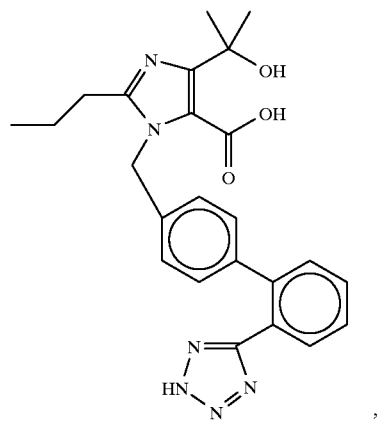

,

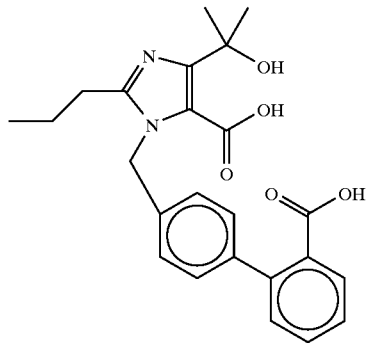

,

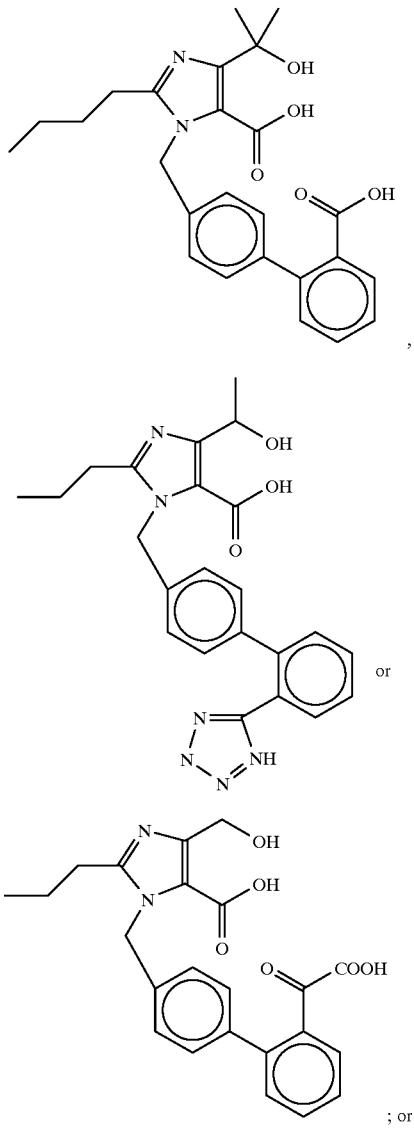

, or

; or

(52) A compound having the following formula:

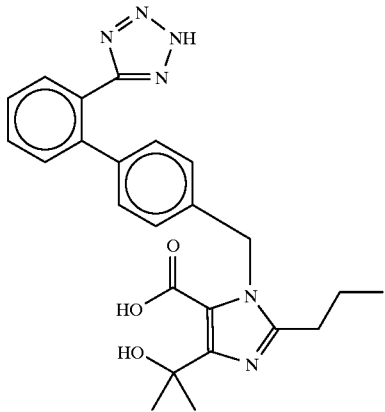

Substituent group (I): an aryl group, a 5- or 6-membered heteroaromatic ring group, a halogen atom, a hydroxyl group, a lower alkoxy group, a carboxyl group, a lower alkoxycarbonyl group, an amino group, an aliphatic acylamide group and an aromatic acylamide group.

In the above general formula (I):

The term "lower alkyl group" used in the definition of $R^1$, $R^2$, $R^5$, $R^7$, $R^8$, $R^9$ and $R^{10}$ and the "lower alkyl group" of the term "lower alkyl group substituted by 1 to 3 substituents selected from Substituent group (I)" used in the definition of $R^9$ and $R^{10}$ signify a straight or branched chain alkyl group containing 1 to 6 carbon atoms such as, for example, methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl; and preferably a straight or branched chain alkyl group containing 1 to 4 carbon atoms. More preferably, $R^1$ and $R^2$ signify a straight or branched chain alkyl group containing 2 to 4 carbon atoms and the term "lower alkyl group" used in the definition of $R^5$, $R^7$, $R^8$, $R^9$ and $R^{10}$ and the "lower alkyl group" of the term "lower alkyl group substituted by 1 to 3 substituents selected from Substituent group (I)" used in the definition of $R^9$ and $R^{10}$ signify a straight chain alkyl group containing 1 or 2 carbon atoms.

The term "lower alkenyl group" used in the definition of $R^1$, $R^2$, $R^7$ and $R^8$ signifies a straight or branched chain alkenyl group containing 2 to 6 carbon atoms such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl; and preferably a straight or branched chain alkenyl group containing 3 to 5 carbon atoms.

The term "cycloalkyl group" used in the definition of $R^5$, $R^7$ and $R^8$ signifies a 3- to 10-membered saturated cyclic hydrocarbon group, which may optionally be a condensed ring group, such as cyclopropyl, cyclobutyl, cyclopentyl, cyclohexyl, cycloheptyl, norbornyl or adamantyl; and preferably a 5- to 10-membered saturated cyclic hydrocarbon group.

The term "aliphatic acyl group" used in the definition of $R^5$ and the "aliphatic acyl group" of the term "aliphatic acylamide group" used in the definition of Substituent group (I) signify an "alkylcarbonyl group" such as, for example, formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl or heneicosanoyl; a "carboxylated alkylcarbonyl group" such as succinoyl, glutaroyl or adipoyl; a "halogeno-lower alkylcarbonyl group" such as chloroacetyl, dichloroacetyl, trichloroacetyl or trifluoroacetyl; a "lower alkoxy-lower alkylcarbonyl group" such as methoxyacetyl; an "unsaturated alkylcarbonyl group" such as (E)-2-methyl-2-butenoyl; and preferably an "alkylcarbonyl group".

The term "lower alkylene group" used in the definition of B signifies a straight or branched chain alkylene group containing 1 to 6 carbon atoms such as, for example, methylene, methylmethylene, ethylene, propylene, trimethylene, tetramethylene, 1-methyltrimethylene, 2-methyltrimethylene, 3-methyltrimethylene, pentamethylene or hexamethylene; preferably a straight or branched chain alkylene group containing 1 to 4 carbon atoms; more preferably methylene, ethylene, trimethylene or tetramethylene; and most preferably methylene or ethylene.

The term "lower alkoxy group" used in the definition of $R^6$ and Substituent group (I) and the "lower alkoxy group" of the term "lower alkoxycarbonyl group" used in the definition of Substituent group (I) signify a group bonded to the aforesaid "lower alkyl group" by an oxygen atom. Examples of lower alkoxy groups include: a straight or branched chain alkoxy group containing 1 to 6 carbon atoms such as, for example, methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy; and preferably a straight or branched chain alkoxy group containing 1 to 4 carbon atoms.

The term "lower alkynyl group" used in the definition of $R^7$ and $R^8$ signifies a straight or branched chain alkynyl group containing 2 to 6 carbon atoms such as ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl; and preferably a straight or branched chain alkynyl group containing 3 to 5 carbon atoms.

The term "aryl group" used in the definition of $R^7$, $R^8$ and Substituent group (I) signifies an aromatic hydrocarbon group containing 5 to 14 carbon atoms such as phenyl, indenyl, naphthyl, phenanthrenyl or anthracenyl; preferably phenyl or naphthyl; and more preferably phenyl.

The aforesaid "aryl group" may optionally be a ring group condensed with a cycloalkyl group containing 3 to 10 carbon atoms. Examples of such groups include, for example, 2-indanyl.

The term "aralkyl group" used in the definition of $R^7$ and $R^8$ signifies a "lower alkyl group" substituted by 1 to 3 aryl groups such as benzyl, phenethyl, 3-phenylpropyl, α-naphthylmethyl, β-naphthylmethyl, diphenylmethyl, triphenylmethyl, 6-phenylhexyl, α-naphthyldiphenylmethyl or 9-anthrylmethyl; a lower alkyl group substituted by 1 to 3 aryl groups, which are substituted by lower alkyl, lower alkoxy, nitro, halogen, cyano and/or alkoxycarbonyl, such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, piperonyl or 4-methoxycarbonylbenzyl; preferably an "aralkyl group" in which a "lower alkyl group" has 1 to 4 carbon atoms; and more preferably an alkyl group containing 1 to 4 carbon atoms substituted by 1 or 2 aryl groups.

The term "5- or 6-membered heteroaromatic ring group" used in the definition of Substituent group (I) signifies a 5- or 6-membered heteroaromatic ring group containing 1 to 3 sulfur atoms, oxygen atoms and/or nitrogen atoms. Examples of such heteroaromatic ring groups include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl or pyrazinyl; preferably a 5- or 6-membered heteroaromatic ring group which contains at least one nitrogen atom and may optionally contain an oxygen atom or a sulfur atom such as, for example, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl or pyrazinyl; and more preferably imidazolyl, oxazolyl, isoxazolyl, thiazolyl, triazolyl, tetrazolyl or pyridyl.

The term "halogen atom" used in the definition of Substituent group (I) signifies fluorine atom, chlorine atom, bromine atom or iodine atom; and preferably fluorine atom or chlorine atom.

The "aromatic acyl group" of the term "aromatic acylamide group" used in the definition of Substituent group (I) signifies, for example, an "arylcarbonyl group" such as benzoyl, α-naphthoyl or β-naphthoyl; a "halogenoarylcarbonyl group" such as 2-bromobenzoyl or 4-chlorobenzoyl; a "lower alkylated arylcarbonyl group" such as 2,4,6-trimethylbenzoyl or 4-toluoyl; a "lower alkoxylated arylcarbonyl group" such as 4-anisoyl; a "carboxylated arylcarbonyl group" such as 2-carboxybenzoyl, 3-carboxybenzoyl or 4-carboxybenzoyl; a "nitrated arylcarbonyl group" such as 4-nitrobenzoyl or 2-nitrobenzoyl; a "lower alkoxycarbonylated arylcarbonyl group" such as 2-(methoxycarbonyl)benzoyl; and an "arylated arylcarbonyl group" such as 4-phenylbenzoyl; and preferably an "arylcarbonyl group".

The term "pharmacologically acceptable salt" signifies the salts which may be produced from a compound of general formula (I) of the present invention. As such salts there come especially into consideration: a metal salt such as an alkaline metal salt (e.g., sodium salt, potassium salt and lithium salt), an alkaline earth metal salt (e.g., calcium salt and magnesium salt), aluminium salt or iron salt; an amine salt such as an inorganic salt (e.g., ammonium salt) or an organic salt (e.g., tert-octylamine salt, dibenzylamine salt, morpholine salt, glucosamine salt, alkyl phenylglycinate salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt and tris(hydroxymethyl)aminomethane salt); an inorganic acid salt such as a hydrohalic acid salt (e.g., hydrochloric acid salt, hydrobromic acid salt and hydroiodic acid salt), nitric acid, sulfuric acid or phosphoric acid; an organic acid salt such as a lower alkanesulfonic acid (e.g., methanesulfonic acid salt, trifluoromethanesulfonic acid salt and ethanesulfonic acid salt), an arylsulfonic acid (e.g., benzenesulfonic acid salt and p-toluenesulfonic acid salt), an acetic acid salt, a malic acid salt, a fumaric acid salt, a succinic acid salt, a citric acid salt, a tartaric acid salt, an oxalic acid salt and a maleic acid salt; and an amino acid salt (e.g., glycine salt, lysine salt, arginine salt, ornithine salt, glutamic acid salt and aspartic acid salt).

When the compounds of formula (I) of the invention are allowed to stand in the atmosphere or recrystallized, they sometimes form a hydrate compound based upon absorbing water or hydrating. The present invention also covers such a salt.

The term "esters or other derivatives" signifies such derivatives that, where the compounds of formula (I) of the present invention have at least one hydroxyl group, can be derived by modifying with a "conventional protecting group" or a "protecting group capable of cleaving by biological methods such as an enzymatic reaction in vivo"; and/or that, where the compounds of formula (I) of the present invention have at least one carboxyl group or carboxycarbonyl group, can be derived by modifying with a "conventional protecting group" or with a "protecting group capable of cleaving by biological methods such as an enzymatic reaction in vivo", or the said term signifies an amide of the said carboxyl group or the said carboxycarbonyl group.

The term "conventional protecting group" signifies a protecting group capable of being removed by chemical methods such as reduction or hydrolysis. As the "conventional protecting group" of a "hydroxyl group" there comes into consideration: the aforesaid "aliphatic acyl grup"; the aforesaid "aromatic acyl group"; a "tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl; a "tetrahydrofuranyl or tetrahydrothiofuranyl group" such as tetrahydrofuran-2-yl or tetrahydrothiofuran-2-yl; a "silyl group" such as a tri(lower alkyl)silyl group (e.)(rimethylsilyl, triethylsilyl, isopropyldimethylsilyl, tert-butyldimethylsilyl, methyldiisopropylsilyl, methyldi-tert-butylsilyl and triisopropylsilyl) or a tri(lower alkyl)silyl group substituted by 1 or 2 aryl groups (e.g diphenylmethylsilyl, diphenylbutylsilyl, diphenylisopropylsilyl and phenyldiisopropylsilyl); an "alkoxymethyl group" such as a lower alkoxymethyl group (e.g. methoxymethyl, 1,1-dimethyl-1-methoxymethyl, ethoxymethyl, propoxymethyl, isopropoxymethyl, butoxymethyl and tert-butoxymethyl), a lower alkoxylated alkoxymethyl group (e.g. 2-methoxyethoxymethyl) or a halogeno-lower alkoxymethyl group (e.g. 2,2,2-trichloroethoxymethyl and bis(2-chloroethoxy)methy); a substituted ethyl group such as a lower alkoxylated ethyl gruop (e.g. 1-ethoxyethyl and 1-(isopropoxy)ethyl) or a halogenated ethyl group (e.g. 2,2,2-trichloroethyl); the aforesaid "aralkyl group"; an "alkoxycarbonyl group" such as a lower alkoxycarbonyl group (e.g. methoxycarbonyl, ethoxycarbonyl, tert-butoxycarbonyl and isobutoxycarbonyl) or a lower alkoxycarbonyl group substituted by halogen or tri(lower alkyl) silyl (e.g. 2,2,2-trichloroethoxycarbonyl and 2-trimethylsilylethoxycarbonyl); an "alkenyloxycarbonyl group" such as vinyloxycarbonyl or allyloxycarbonyl; and an "aralkyloxycarbonyl group" which may optionally be substituted by 1 or 2 lower alkoxy or nitro groups such as benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl.

As the "conventional protecting group" of a "carboxyl group or carboxycarbonyl group" there come especially into consideration: the aforesaid "lower alkyl group"; the aforesaid "lower alkenyl group"; the aforesaid "lower alkynyl group"; a "halogeno-lower alkyl group" such as 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl; a hydroxy-"lower alkyl group" such as 2-hydroxyethyl, 2,3-dihydroxypropyl, 3-hydroxypropyl, 3,4-dihydroxybutyl or 4-hydroxybutyl; an "aliphatic acyl-lower alkyl group" such as acetylmethyl; the aforesaid "aralkyl group"; and the aforesaid "silyl group".

The term "protecting group capable of cleaving by biological methods such as an enzymatic reaction in vivo" signifies a protecting group capable of cleaving by biological methods such as an enzymatic reaction in vivo to produce a free acid or its salt. In order to determine whether a compound is such a derivative or not, one can administer the compound orally or intravenously to an experimental animal such as a rat or mouse followed by examining the body fluids of the animal to detect and determine an original compound or pharmacologically acceptable salt.

As the "protecting group capable of cleaving by biological methods such as an enzymatic reaction in vivo" of a hydroxyl group there come into consideration, for example, a "1-(acyloxy)-lower alkyl group" such as a "1-(aliphatic acyloxy)-lower alkyl group" (e.g. formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl), a "1-(cycloalkylcarbonyloxy)-lower alkyl group" (e.g. cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl), a "1-(aromatic acyloxy)-lower alkyl group" (e.g. benzoyloxymethyl) or the like; a "1-(alkoxycarbonyloxy)alkyl group" such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, cyclopentyloxycarbonyloxymethyl, hexyloxycarbonyloxymethyl, cyclohexyloxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(tert-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy) propyl, 1-(ethoxycarbonyloxy)propyl, 1-(propoxycarbonyloxy)propyl, 1-(isopropoxycarbonyloxy) propyl, 1-(butoxycarbonyloxy)propyl, 1-(isobutoxycarbonyloxy)propyl, 1-(pentyloxycarbonyloxy) propyl, 1-(hexyloxycarbonyloxy)propy, 1-(methoxycarbonyloxy)butyl, 1-(ethoxycarbonyloxy) butyl, 1-(propoxycarbonyloxy)butyl, 1-(isopropoxycarbonyloxy)butyl, 1-(butoxycarbonyloxy)

butyl, 1-(isobutoxycarbonyloxy)butyl, 1-(methoxycarbonyloxy)pentyl, 1-(ethoxycarbonyloxy) pentyl, 1-(methoxycarbonyloxy)hexyl or 1-(ethoxycarbonyloxy)hexyl; a "2-oxo-1,3-dioxolenylmethyl group" such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methyl; a "phthalidyl group" such as phthalidyl, dimethylphthalidyl or dimethoxyphthalidyl; the aforesaid "aliphatic acyl group"; the aforesaid "aromatic acyl group"; a "half ester salt residue of succinic acid"; "an amino acid residue capable of forming an ester"; a carbamoyl group; a carbamoyl group substituted by 1 or 2 lower alkyl groups; a "1-(acyloxy)alkyloxycarbonyl group" such as pivaloyloxymethyloxycarbonyl; and preferably a "2-oxo-1,3-dioxolenylmethyl group", "phthalidyl group", "aliphatic acyl group" or "aromatic acyl group".

As the "protecting group capable of cleaving by biological methods such as an enzymatic reaction in vivo" of a "carboxyl group or carboxycarbonyl group" there come especially into consideration: an "alkoxy-lower alkyl group" such as a lower alkoxy-lower alkyl group (e.g. methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, n-propoxymethyl, isopropoxymethyl, n-butoxymethyl and tert-butoxymethyl); a lower alkoxylated lower alkoxy-lower alkyl group (e.g. 2-methoxyethoxymethyl); an "aryloxy-lower alkyl group" (e.g. phenoxymethyl); a halogenated lower alkoxy-lower alkyl group (e.g. 2,2,2-trichloroethoxymethyl and bis(2-chloroethoxy)methyl) or the like; a "lower alkoxycarbonyl-lower alkyl group" such as methoxycarbonylmethyl; a "cyano-lower alkyl group" such as cyanomethyl or 2-cyanoethyl; a "lower alkylthiomethyl group" such as methylthiomethyl or ethylthiomethyl; an "arylthiomethyl group" such as phenylthiomethyl or naphthylthiomethyl; a "lower alkylsulfonyl-lower alkyl group which may optionally be substituted by halogen" such as 2-methanesulfonylethyl or 2-trifluoromethanesulfonylethyl; an "arylsulfonyl-lower alkyl group" such as 2-benzenesulfonylethyl or 2-toluenesulfonylethyl; the aforesaid "1-(acyloxy)-lower alkyl group"; the aforesaid "phthalidyl group"; the foresaid "aryl group"; the aforesaid "lower alkyl group"; a "carboxylalkyl group" such as carboxymethyl; an "amino acid residue capable of forming an amide" such as phenylalanine; and preferably an "alkoxy-lower alkyl group", a "1-(acyloxy)-lower alkyl group", a "phthalidyl group", a "lower alkyl group" or an "amino acid residue capable of forming an amide".

The compounds comprised in the composition in accordance with the present invention can exist in the form of various stereoisomers due to the presence of an asymmetric carbon atom having R- or S-configuration in the molecule. But the present invention covers both the individual isomers and mixtures thereof.

All compounds of the present invention, which are ocular tension lowering agents and/or glaucoma therapeutic agents for eye drops, which are submitted to the use as a ocular tension lowering agent and/or a glaucoma therapeutic agent for eye drops and which are used in a method of medical treatment of ocular hypertension and/or glaucoma diseases, are known and can be synthesized following the procedure disclosed in, for example, (1) Japanese Patent Kokai Application No. Hei 5-78328, (2) Japanese Patent Kokai Application No. Hei 6-49036, (3) EP 245637A, (4) EP 253310A, (5) EP 291969A, (6) EP 323841A, (7) EP 324377A, (8) EP 380959A, (9) EP 392317A, (10) EP 399731A, (11) EP 399732A, (12) EP 400835A, (13) EP 400974A, (14) EP 401030A, (15) EP 403158A, (16) EP 403159A, (17) EP 407102A, (18) EP 407342A, (19) EP 409332A, (20) EP 411507A, (21) EP 411766A, (22) EP 412594A, (23) EP 412848A, (24) EP 415886A, (25) EP 419048A, (26) EP 420237A, (27) EP 424317A, (28) EP 425211A, (29) EP 425921A, (30) EP 426021A, (31) EP 427463A, (32) EP 429257A, (33) EP 430300A, (34) EP 430709A, (35) EP 432737A, (36) EP 434038A, (37) EP 434249A, (38) EP 435827A, (39) EP 437103A, (40) EP 438869A, (41) EP 442473A, (42) EP 443568A, (43) EP 443983A, (44) EP 445811A, (45) EP 446062A, (46) EP 447342A, (47) EP 449699A, (48) EP 450566A, (49) EP 453210A, (50) EP 454511A, (51) EP 455423A, (52) EP 456442A, (53) EP 456510A, (54) EP 459136A, (55) EP 461039A, (56) EP 461040A, (57) EP 465323A, (58) EP 465368A, (59) EP 467207A, (60) EP 467715A, (61) EP 468372A, (62) EP 468470A, (63) EP 470543A, (64) EP 470794A, (65) EP 470795A, (66) EP 475206A, (67) EP 475898A, (68) EP 479479A, (69) EP 480204A, (70) EP 480659A, (71) EP 481448A, (72) EP 481614A, (73) EP 483683A, (74) EP 485929A, (75) EP 487252A, (76) EP 487745A, (77) EP 488532A, (78) EP 490587A, (79) EP 490820A, (80) EP 495626A, (81) EP 495627A, (82) EP 497121A, (83) EP 497150A, (84) EP 497516A, (85) EP 503162A, (86) EP 510812A, (87) U.S. Pat. No. 4,340,598, (88) U.S. Pat. No. 4,355,042, (89) U.S. Pat. No. 4,820,843, (90) U.S. Pat. No. 4,870,186, (91) U.S. Pat. No. 4,874,867, (92) U.S. Pat. No. 4,880,804, (93) U.S. Pat. No. 4,916,129, (94) U.S. Pat. No. 5,015,651, (95) U.S. Pat. No. 5,039,814, (96) U.S. Pat. No. 5,041,552, (97) U.S. Pat. No. 5,043,349, (98) U.S. Pat. No. 5,045,540, (99) U.S. Pat. No. 5,0495,65, (100) U.S. Pat. No. 5,053,329, (101) U.S. Pat. No. 5,057,522, (102) U.S. Pat. No. 5,064,825, (103) U.S. Pat. No. 5,066,586, (104) U.S. Pat. No. 5,081,127, (105) U.S. Pat. No. 5,087,634, (106) U.S. Pat. No. 5,087,702, (107) U.S. Pat. No. 5,093,346, (108) U.S. Pat. No. 5,098,920, (109) U.S. Pat. No. 5,100,897, (110) U.S. Pat. No. 5,102,880, (111) U.S. Pat. No. 5,104,891, (112) U.S. Pat. No. 5,126,342, (113) U.S. Pat. No. 5,128,327, (114) U.S. Pat. No. 5,128,356, (115) U.S. Pat. No. 5,130,318, (116) U.S. Pat. No. 5,130,439, (117) U.S. Pat. No. 5,137,906, (118) U.S. Pat. No. 5,138,069, (119) WO 8906233, (120) WO 9100277, (121) WO 9100281, (122) WO 9107404, (123) WO 9111909, (124) WO 9111999, (125) WO 9112001, (126) WO 9112002, (127) WO 9113063, (128) WO 9114367, (129) WO 9114679, (130) WO 9115206, (131) WO 9115209, (132) WO 9115479, (133) WO 9115479, (134) WO 9116313, (135) WO 9117148, (136) WO 9118888, (137) WO 9119697, (138) WO 9119715, (139) WO 9200067, (140) WO 9200068, (141) WO 9200285, (142) WO 9200977, (143) WO 9202257, (144) WO 9202508, (145) WO 9202510, (146) WO 9204335, (147) WO 9204343, (148) WO 9205161, (149) WO 9206081, (150) WO 9207852, (151) WO 9210179, (152) WO 9210180, (153) WO 9210181, (154) WO 9210182, (155) WO 9210183, (156) WO 9210184, (157) WO 9210185, (158) WO 9210186, (159) WO 9210187, (160) WO 9210188 and (161) WO 9211255; preferably Japanese Patent Kokai Application No. Hei 5-78328 and 6-49036.

The "esters and other derivatives" of a carboxyl group and/or a carboxycarbonyl group can be prepared from the corresponding carboxylic acid salts or free carboxylic acids as follows:

Where the said protecting reaction is alkylation, it is conducted in accordance with one of following methods:

Method 1

The method is to react a compound of general formula (I) having at least one carboxyl group and/or one carboxycarbonyl group with a compound of general formula: $R^{11}$—X in a solvent in the presence of a base, normally, at a temperature of —20° C. to 120° C. (preferably 0° C. to 80° C.) for a period of 0.5 to 10 hours.

In the above formula, $R^{11}$ represents a residue of the corresponding esters or other derivatives; and X represents a group capable of leaving as a nucleophilic group. Examples of such groups include, for example, a halogen atom such as chlorine, bromine or iodine; a lower alkanesulfonyloxy groups such as methanesulfonyloxy or ethanesulfonyloxy; halogeno-lower alkanesulfonyloxy groups such as trifluoromethanesulfonyloxy or pentafluoroethanesulfonyloxy; and arylsulfonyloxy groups such as benzenesulfonyloxy, p-toluenesulfonyloxy or p-nitrobenzenesulfonyloxy.

As the compounds having a general formula: $R^{11}$—X there come into consideration, for example: aliphatic acyloxymethyl halides such as acetoxymethyl chloride, pivaloyloxymethyl bromide or pivaloyloxymethyl chloride; lower alkoxycarbonyloxyalkyl halides such as ethoxycarbonyloxymethyl chloride, isopropoxycarbonyloxymethyl chloride, 1-(ethoxycarbonyloxy)ethyl chloride or 1-(ethoxycarbonyloxy)ethyl iodide; phthalidyl halides; and (5-methyl-2-oxo-1,3-dioxolen-4-yl)methyl halides.

There is no particular limitation upon the nature of the solvent used, provided that it has no adverse effect upon the reaction and can dissolve the starting material at some extent. Examples of preferred solvents include: aliphatic hydrocarbons such as hexane or heptane; aromatic hydrocarbons such as benzene, toluene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane, diethylene glycol diemthyl ether; ketones such as acetone, methyl ethyl ketone or methyl isobutyl ketone; nitriles such as acetonitrile; and amides such as formamide, N,N-dimethylformamide, N,N-dimethylacetamide, N-methyl-2-pyrrolidone, N-methylpyrrolidinone or hexamethylphosphoric triamide.

There is no particular limitation upon the nature of the base used, provided that it can be used as a base in normal reaction. Examples of preferred bases include: inorganic bases such as alkaline metal carbonates (e.g. sodium carbonate, potassium carbonate and lithium carbonate), alkaline metal hydrogencarbonates (e.g. sodium hydrogencarbonate, potassium hydrogencarbonate and lithium hydrogencarbonate), alkaline metal hydrides (e.g. lithium hydride, sodium hydride and potassium hydride), alkaline metal hydroxides (e.g. sodium hydroxide, potassium hydroxide, barium hydroxide and lithium hydroxide), or alkaline metal fluorides (e.g. sodium fluoride and potassium fluoride); alkaline metal alkoxides such as sodium methoxide, sodium ethoxide, potassium methoxide, potassium ethoxide, potassium tert-butoxide or lithium methoxide; organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene, 1,4-diazabicyclo[2.2.2]octane or 1,8-diazabicyclo(5.4.0]undec-7-ene; and organic metal bases such as butyllithium, lithium diisopropylamide or lithium bis(trimethylsilyl)amide.

Method 2

This method is to react a compound of general formula (I) having at least one carboxyl group and/or one carboxycarbonyl group with a compound of general formula: $R^{11}$—OH (in which $R^{11}$ is as defined above) in a solvent in the presence or absence of a base under the influence of a condensing agent.

There is no particular limitation upon the nature of the solvent used, provided that it has no adverse effect upon the reaction and can dissolve the starting material at some extent. Examples of preferred solvents include: aliphatic hydrocarbons such as hexane or heptane; aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane, diethylene glycol dimethyl ether; nitriles such as acetonitrile or isobutyronitrile; amides such as formamide, N,N-dimethylformamide, N,N-dimethylacetamide, N-methyl-2-pyrrolidone, N-methylpyrrolidinone or hexamethylphosphoric triamide.

There is no particular limitation upon the nature of the base used, provided that it can be used as a base in normal reaction. Examples of preferred bases include: organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline and N,N-diethylaniline.

As the condensing agents to be used there come into consideration:

(1) A combination of phosphates such as diphenylphosphoryl azide or diethyl cyanophosphate and the aforesaid base;

(2) Carbodiimides such as 1,3-dicyclohexylcarbodiimide, 1,3-diisopropylcarbodiimide or 1-ethyl-3-(3-dimethylaminopropyl)carbodiimide;

(3) A combination of the aforesaid carbodiimides and the aforesaid bases;

(4) A combination of the aforesaid carbodiimides and N-hydroxy derivatives such as N-hydroxysuccinimide, 1-hydroxybenzotriazole or N-hydroxy-5-norbornene-2,3-dicarboximide;

(5) A combination of disulfides such as 2,2'-dipyridyl disulfide or 2,2'-dibenzothiazolyl disulfide and phosphines such as triphenylphosphine or tributylphosphine;

(6) Carbonates such as N,N'-disuccinimidyl carbonate, di-2-pyridyl carbonate or S,S'-bis(1-phenyl-1H-tetrazol-5-yl) dithiocarbonate;

(7) Phosphinic chlorides such as N,N'-bis(2-oxo-3-oxazolidinyl)phosphinic chloride;

(8) Oxalates such as N,N'-disuccinimidyl oxalate, N,N'-diphthalimide oxalate, N,N'-bis(5-norbornene-2,3-dicarboxyimidyl) oxalate, 1,1'-bis(benzotriazolyl) oxalate, 1,1'-bis(6-trifluoromethylbenzotriazolyl) oxalate;

(9) A combination of the aforesaid phosphines and azodicarboxylates or azodicarboxyamides such as diethyl azodicarboxylate or 1,1'-(azodicarbonyl)dipiperidine;

(10) A combination of the aforesaid phosphines and the aforesaid bases;

(11) N-lower alkyl-5-arylisoxazolium-3'-sulfonates such as N-ethyl-5-phenylisoxazolium-3'-sulfonate;

(12) Diheteroaryl diselenides such as di-2-pyridyl diselenide;

(13) Arylsulfonyl triazolides such as p-nitrobenzenesulfonyl triazolide;

(14) 2-Halogeno-1-lower alkylpyridinium halides such as 2-chloro-1-methylpyridinium iodide;

(15) Imidazoles such as 1,1'-oxalyldiimidazole or N,N'-carbonyldiimidazole;

(16) 3-Lower alkyl-2-halobenzothiazolium fluoroborates such as 3-ethyl-2-chlorobenzothiazolium fluoroborate;

(17) 3-Lower alkylbenzothiazole-2-selones such as 3-methylbenzothiazole-2-selone;

(18) Phosphates such as phenyl dichlorophosphate or polyphosphate;

(19) Halogenosulfonyl isocyanates such as chlorosulfonyl isocyanate;

(20) Halogenosilanes such as trimethylsilyl chloride or triethylsilyl chloride;

(21) A combination of lower alkanesulfonyl halides such as methanesulfonyl chloride and the bases shown below;

(22) N,N,N',N'-tetra(lower alkyl)halogenoformamidium chlorides such as N,N,N',N'-tetramethylchloroformamidium chloride; and preferably carbodiimides or a combination of phosphines and azodicarboxylates or azodicarboxyamides.

The reaction can also be carried out using a catalytic amount of 4-(N,N-dimethylamino)pyridine or 4-pyrrolidinopyridine together with other bases. In order to conduct effectively the reaction, dehydrating agents such as molecular sieves; quaternary ammonium salts such as benzyltriethylammonium chloride or tetrabutylammonium chloride; crown ethers such as dibenzo-18-crown-6; acid-capturing agents such as 3,4-dihydro-2H-pyrido[1,2-a]pyrimidin-2-one or the like can be added to the reaction mixture.

The reaction is carried out at a temperature of from $-20°$ C. to $80°$ C., preferably $0°$ C. to room temperature.

The time required for the reaction varies mainly depending upon the reaction temperature as well as upon the nature of the starting material, the reagent and the solvent used, but the reaction is normally completed within a period of 10 minutes to 3 days, preferably 30 minutes to 1 day.

Method 3

The method is to react a compound of general formula (I) having at least one carboxyl group and/or one carboxycarbonyl group with the corresponding alcohol such as methanol, ethanol, propanol or butanol in a solvent in the presence of an acid catalyst.

There is no particular limitation upon the nature of the solvent used, provided that it has no adverse effect upon the reaction and can dissolve the starting material at some extent. Examples of preferred solvents include: the same alcohol as the reagent used; aliphatic hydrocarbons such as hexane or heptane; aromatic hydrocarbons such as benzene, toluene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane, diethylene glycol dimethyl ether; and preferably the same alcohol as the reagent used.

There is no particular limitation upon the nature of the acid catalyst used, provided that it can be used as an acid catalyst in normal reaction. Examples of preferred acid catalysts include: Bronsted acid such as inorganic acids (e.g. hydrogen chloride, hydrobromic acid, sulfuric acid, perchloric acid and phosphoric acid) or organic acids (e.g. acetic acid, formic acid, oxalic acid, methanesulfonic acid, p-toluenesulfonic acid, trifluoroacetic acid and trifluoromethanesulfonic acid); Lewis acids such as boron trichloride, boron trifluoride or boron tribromide; and acidic ion-exchange resin.

The reaction is carried out at a temperature of from $0°$ C. to $100°$ C., preferably $20°$ C. to $60°$ C.

The time required for the reaction varies mainly depending upon the reaction temperature as well as upon the nature of the starting material, the reagent and the solvent used, but the reaction is normally completed within a period of from 1 to 24 hours.

Method 4

The method is to react a compound of general formula (I) having at least one carboxyl group and/or one carboxycarbonyl group with (1) a halogenating agent (for example, phosphorus pentachloride, thionyl chloride, oxalyl chloride and the like) at near room temperature for a period of 30 minutes to 5 hours to produce an acid halide, or with (2) chloroformates such as methyl chloroformate or ethyl chloroformates (e.g. methyl chloroformate and ethyl chloroformate) in the presence of an organic base such as triethylamine to produce a mixed acid anhydride, and then reacting the product with the corresponding alcohol in an inert solvent in the presence of a base (e.g. triethylamine) at a temperature of from $-10°$ C. to $150°$ C. (preferably at near room temeperature) for a period of from 10 minutes to 15 hours (preferably 30 minutes to 10 hours).

There is no particular limitation upon the nature of the inert solvent used, provided that it has no adverse effect upon the reaction and can dissolve the starting material to some extent. Examples of preferred solvent include: aromatic hydrocarbons such as benzene, toluene or xylene; halogenated hydrocarbons such as dichloromethane or chloroform; esters such as ethyl acetate or propyl acetate; ethers such as ether, tetrahydrofuran, dioxane or dimethoxyethane; and nitrites such as acetonitrile.

Method 5

The method is to react a compound of general formula (I) having at least one carboxyl group and/or one carboxycarbonyl group with a diazoalkane such as diazomethane or diazoethane (generally an ether solution of diazoalkane) at near room temperature (depending on the reaction system, if necessary, upon heating).

Method 6

Furthermore, where the protecting reaction is lower alkylation, it can be conducted by reacting a compound of general formula (I) having at least one carboxyl group and/or one carboxycarbonyl group with a dialkyl sulfate such as dimethyl sulfate or diethyl sulfate by conventional means in the presence of a similar base to that described in Method 1.

After completion of the reaction, the desired compound can be recovered from the reaction mixture by conventional means.

An example of such technique comprises: neutralizing properly the reaction mixture; or filtering off where insoluble materials exist; adding water and a water-immiscible solvent such as ethyl acetate; washing the organic phase with water; separating the organic phase comprising the desired compound; drying over anhydrous magnesium sulfate or the like; and finally distilling off the solvent.

If necessary, the compounds thus obtained can be further separated and purified by conventional means, for example, recrystallization, reprecipitation or by the proper combination of conventional means for separating and purifying organic compounds, for example, absorption chromatography through a carrier such as silica gel, alumina or Florisil (magnesium-silica gel) and partition chromatography through a carrier such as Cephadex LH-20 (a product of Pharmacia Inc.), Amberlite XAD-11 (a product of Rohm & Haas Co.) or Diaion HP-20 (a product of Mitsubishi Kasei Co.) by eluting using an apropriate eluting solution.

The reaction for preparing the salt of carboxylic acid:

(1) In the case of metal salts of a carboxylic acid, the desired metal salts can be prepared by reacting a compound of general formula (I) having at least one carboxyl group and/or one carboxycarbonyl group with the hydroxides, carbonates or the like of the said metal in an aqueous solvent.

Examples of the aqueous solvents used include: water; alcohols such as methanol or ethanol; acetone; a mixture of water and one or more of these organic solvents; and preferably a mixture of a hydrophilic organic solvent and water.

The reaction can usually be conducted at near room temperature, if necessary, upon heating.

(2) In the case of amine salts of a carboxylic acid, the desired amine salts can be prepared by reacting a compound of general formula (I) having at least one carboxyl group and/or one carboxycarbonyl group with the corresponding amine in a solvent by conventional means.

Examples of the solvents used include: water; alcohols such as methanol or ethanol; ethers such as tetrahydrofuran; nitrites such as acetonitrile; a mixture of water and one or more of these solvents; and preferably alcohols.

(3) In the case of amino acid salts of a carboxylic acid, the desired amino acid salts can be prepared by reacting a compound of general formula (I) having at least one free carboxyl group with the corresponding amino acid in an aqueous solvent.

Examples of the aqueous solvents used include: water; alcohols such as methanol or ethanol; ethers such as tetrahydrofuran; and a mixture of water and one or more of these solvents.

The reaction can usually be conducted upon heating, preferably at a temperature of from 50° C. to 60° C.

The esters or other derivatives of a hydroxyl group can be produced from the corresponding compound as follows.

It is conducted in accordance with one of following methods:

Method A

The method is to react a compound of general formula (I) having at least one hydroxyl group with 1 to 4 equivalents (preferably 2 to 3 equivalents) of a compound of formula; $R^{12}$—X' or $R^{12}$—O—R , wherein $R^{12}$ represents an acyl group, in a solvent in the presence or absence of a base.

In the above formulae, $R^{12}$ represents the corresponding residue of esters or other derivatives; and X' represents a leaving group. There is no particular limitation upon the nature of the leaving group, provided that it is generally capable of leaving as a nucleophilic group. Examples of preferred leaving groups include: a halogen atom such as chlorine, bromine or iodine; a lower alkoxycarbonyloxy group such as methoxycarbonyloxy or ethoxycarbonyloxy; a halogenated alkylcarbonyloxy group such as chloroacetyloxy, dichloroacetyloxy, trichloroacetyloxy or trifluoroacetyloxy; a lower alkanesulfonyloxy group such as methanesulfonyloxy or ethanesulfonyloxy; a halogeno-lower alkanesulfonyloxy group such as trifluoromethanesulfonyloxy or pentafluoroethanesulfonyloxy; an arylsulfonyloxy group such as benzenesulfonyloxy, p-toluenesulfonyloxy or p-nitrobenzenesulfonyloxy; and more preferably a halogen atom, a halogeno-lower alkanesulfonyloxy or arylsulfonyloxy group.

As examples of a compound having general formula: $R^{12}$—X there come into consideration: acyl halides such as aliphatic acyl halides (e.g. acetyl chloride, propionyl chloride, butyryl chloride, valeryl chloride and hexanoyl chloride), lower alkoxycarbonyl halides (e.g. methoxycarbonyl chloride, methoxycarbonyl bromide, ethoxycarbonyl chloride, propoxycarbonyl chloride, butoxycarbonyl chloride and hexyloxycarbonyl chloride) or arylcarbonyl halides (e.g. benzoyl chloride, benzoyl bromide and naphthoyl chloride); silyl halides such as trimethylsilyl chloride or triethylsilyl bromide; aralkyl halides such as benzyl chloride or benzyl bromide; and carbonyloxy-lower alkyl halides such as pivaloyloxymethyl chloride or ethoxycarbonyloxymethyl chloride.

As examples of a compound having general formula: $R^{12}$—O—$R^{12}$ there come into consideration: aliphatic carboxylic acid anhydrides such as acetic anhydride, propionic anhydride, valeric anhydride or hexanoic anhydride and mixed acid anhydrides such as acetic formic anhydride.

There is no particular limitation upon the nature of the solvent used, provided that it has no adverse effect upon the reation and can dissolve the starting material to some extent. Examples of preferred solvents include: aliphatic hydrocarbons such as hexane or heptane; aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane, diethylene glycol dimethyl ether; nitriles such as acetonitrile or isobutyronitrile; amides such as formamide, N,N-dimethylformamide, N,N-dimethylacetamide, N-methyl-2-pyrrolidone, N-methylpyrrolidinone or hexamethylphosphoric triamide.

There is no particular limitation upon the nature of the base used, provided that it can be used as a base in normal reaction. Examples of preferred bases include: organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-buyl)-4-methylpyridine, quinoline, N,N-dimethylaniline or N,N-diethylaniline.

The reaction can also be carried out using a catalytic amount of 4-(N,N-dimethylamino)pyridine or 4-pyrrolidopyridine together with other bases. In order to conduct effectively the reaction, quaternary ammonium salts such as benzyltriethylammonium chloride or tetrabutylammonium chloride; crown ethers such as dibenzo-18-crown-6 or the like can be added to the reaction mixture.

The reaction is normally carried out at a temperature of −20° C. to reflux temperature of the solvent used, preferably 0° C. to reflux temperature of the solvent used.

The time required for the reaction varies mainly depending upon the reaction temperature as well as the nature of the starting material, the base and the solvent used, but the reaction is generally completed within a period of 10 minutes to 3 days, preferably 1 to 6 hours.

Method B

The method is to react a compound of general formula (I) having at least one hydroxyl group with a compound of general formula: $R^{12}$—OH, wherein $R^{12}$ signifies an acyl group, and, in the above formula, $R^{12}$ is as defined above, in a solvent in the presence or absence of a base under the influence of the aforesaid "condensing agent".

The solvent to be used is the same one as those used in Method 2.

The base to be used is the same one as those used in Method A.

The reaction is carried out at a temperature of −20° C. to 80° C., preferably 0° C. to room temperature.

The time required for the reaction varies mainly depending upon the reaction temperature as well as the nature of the starting material, the base and the solvent used, but the reaction is generally complete within a period of 10 minutes to 3 days, preferably 30 minutes to 1 day.

Method C

The method is to react a compound of general formula (I) having at least one hydroxyl group with a compound of general formula: $R^{12}$—OH, wherein $R^{12}$ signifies an acyl group and, in the above formula, $R^{12}$ is as defined above, in a solvent in the presence of dialkyl halogenated phosphate such as diethyl chlorophosphate and a base.

The solvent to be used is the same one as those used in Method 3.

The base to be used is the same one as those used in Method A.

The reaction is carried out at a temperature of 0° C. to reflux temperature of the solvent used, preferably room temperature to 50° C.

The time required for the reaction varies mainly depending upon the reaction temperature as well as the nature of the starting material, the reagent and the solvent used, but the reaction is generally completed within a period of 10 minutes to 3 days, preferably 30 minutes to 1 day.

Method D:

The method is to react a compound of general formula (I) having at least one hydroxyl group, in case of lower alkylation, with dialkyl sulfates such as dimethyl sulfate or diethyl sulfate in the presence of a base.

The base used is preferably alkali metal hydrides such as sodium hydride, potassium hydride or lithium hydride.

The reaction is carried out at a temperature of 0° C. to 120° C. (preferably 20° C. to 80° C.) and completed within a period of 1 to 24 hours (preferably 1 to 16 hours).

After completion of the reaction, the desired compound can be recovered from the reaction mixture by conventional means. One example of such technique include: neutralizing appropriately the reaction mixture; or filtering off where insoluble materials exist; adding water and a water-immiscible organic solvent such as ethyl acetate; separating the organic phase comprising the desired compound after washing; drying over anhydrous magnesium sulfate or the like; and finally distilling off the solvent.

The desired compound thus obtained can be separated and purified by conventional means, for example, recrystallization, reprecipitation or by proper combination of conventional means for separating and purifying organic compounds, for example, absorption chromatography through a carrier such as silica gel, alumina or Florisil (magnesium-silica gel) and partition chromatography through a carrier such as Cephadex LH-20 (a product of Pharmacia Inc.), Amberlite XAD-11 (a product of Rohm & Haas Co.) or Diaion HP-20 (a product of Mitsubishi Kasei Co.).

EFFECT OF INVENTION

[Experimental method]

New Zealand white rabbits each weighing 2 to 3 kg were used.

According to the method reported by Kurihara et al. [Ophthalmologic Pharmacology 4, 62–64, (1990)], an ocular hypertension model was prepared to examine the ocular tension lowering effect of the test compounds. After general anaesthesia with urethane, the ocular tension of the test rabbit was determined by use of a tonometer (Alcon Applanation Pneumatonography).

After a local anaesthetic was applied to the rabbit eye by dropping, 0.1 ml of 5% sodium chloride solution was injected into the vitreous body through a 30-gauge injection needle. At the time, 30 minutes after injection, when ocular hypertension was confirmed, 50 $\mu$l of a sample solution was applied by dropping. Then, the ocular tension was determined over 2 hours at intervals of 30 minutes.

[Result]

The area (AUC) between the ocular tension curve obtained from the control group (without drug application) and that obtained from the drug application group, and the maximum value of the lowered ocular tension were calculated to regard as the indices of ocular tension lowering effect.

As can be seen in Table 1, the compositions of the present invention showed an excellent ocular hypertension improving effect.

TABLE 1

Ocular tension lowering effect

| Compound | Applied concentration (%) | AUC (mmHg · hr) | Maximum value of the lowered ocular tension (mmHg) |
| --- | --- | --- | --- |
| Compound A | 1.0 | 11.18 | 9.8 |
| Compound B | 1.0 | 3.21 | 2.6 |
| Compound C | 1.0 | 3.98 | 2.7 |
| Compound D | 0.2 | 6.21 | 6.4 |
| Compound E | 1.0 | 4.90 | 7.6 |
| Compound F | 1.0 | 4.93 | 4.7 |
| Compound G | 1.0 | 5.45 | 8.6 |
| Compound H | 1.0 | 5.58 | 8.6 |
| Compound I | 1.0 | 5.33 | 7.3 |
| DUP 753 | 1.0 | 0.28 | 1.3 |
| DUP 753 | 3.0 | 2.38 | 3.5 |

TABLE 1-continued
| | Ocular tension lowering effect | | |
|---|---|---|---|
| Compound | Applied concentration (%) | AUC (mmHg·hr) | Maximum value of the lowered ocular tension (mmHg) |
Compound A
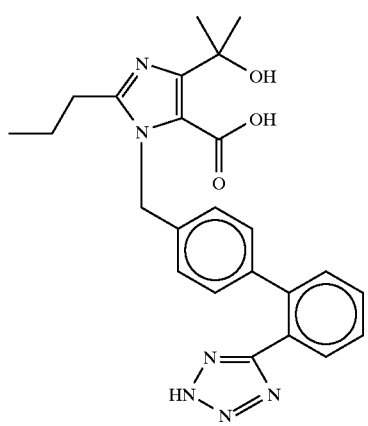
Compound B
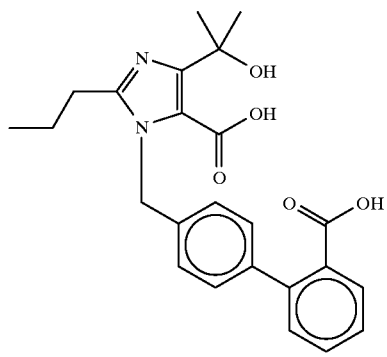
Compound C
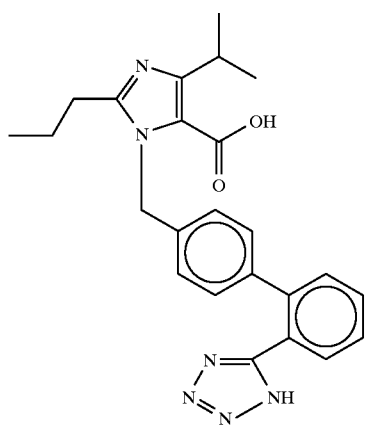
TABLE 1-continued
| | Ocular tension lowering effect | | |
|---|---|---|---|
| Compound | Applied concentration (%) | AUC (mmHg·hr) | Maximum value of the lowered ocular tension (mmHg) |
Compound D
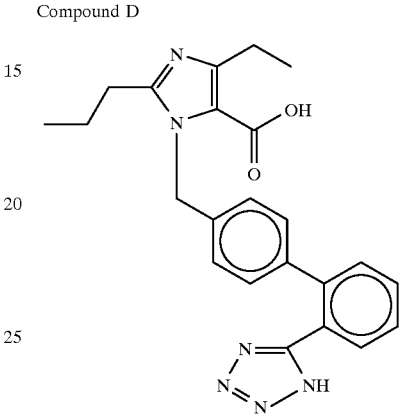
Compound E
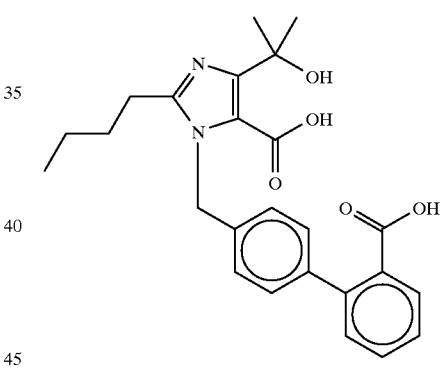
Compound F
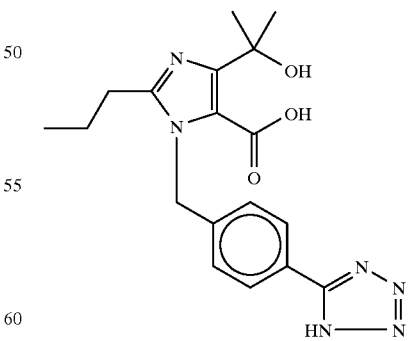

TABLE 1-continued

Ocular tension lowering effect

| Compound | Applied concentration (%) | AUC (mmHg · hr) | Maximum value of the lowered ocular tension (mmHg) |
|---|---|---|---|
| Compound G | | | |
| Compound H | | | |
| Compound I | | | |

[Possible utility in industry]

As mentioned above, since the novel compositions for eye drops of the present invention have an excellent ocular tension lowering activity and no toxicity, the compositions are useful as an ocular tension lowering agent and/or as a glaucoma therapeutic agent.

Additionally, since the novel compositions for eye drops of the present invention have an excellent ocular tension lowering activity and no toxicity, use of the compositions as an ocular tension lowering agent and/or as a glaucoma therapeutic agent is advantageous.

In addition to the above, since the novel compositions for eye drops of the present invention have an excellent ocular tension lowering activity and no toxicity, administration of the compositions to mammalians for the therapy of ocular hypertension and/or glaucoma is useful.

When the compositions of the present invention are desired to be administered, these may be administered in drug composition forms for ophthalmologic use which are suitable for local application to the eyes such as solutions, suspensions, gels, ointments and solid inserts.

These drug compositions can contain from the lowest limit of 0.01%, preferably from 0.1%, to the highest limit of 10%, preferably to 5%, of the active ingredient.

In addition to the compound of the present invention, the composition can contain a β-blocker such as timolol maleate or a parasympathomimetic agent such as pilocarpine.

Any non-toxic inorganic or organic carrier for pharmaceutical use can preferably be mixed to form the drug preparation containing the active composition.

As typical pharmaceutically acceptable carriers, there may be mentioned: water; a mixed solvent of water with a water-miscible solvent such as a lower alkanol or aralkanol; a vegetable oil; a polyalkyleneglycol; a jelly which is based on petroleum; ethylcellulose; ethyl oleate; carboxymethylcellulose; polyvinylpyrrolidone; isopropyl myristate; and other pharmaceutically acceptable carriers which can be used preferably. The pharmaceutical preparation can contain non-toxic additives including emulsifiers, antiseptics, wetting agents and vehicles; for example, polyethyleneglycol 200, 300, 400 and 600; carbowax 1000, 1500, 4000, 6000 and 10000; p-hydroxybenzoates such as methyl p-hydroxybenzoate and propyl p-hydroxybenzoate; quaternary ammonium compounds which are known to have a bactericidal effect and no toxity in use (e.g. benzethonium chloride and benzalkonium chloride); antibacterial drugs such as phenyl mercurate; thimerosal; methylparabene; propylparabene; benzyl alcohol; phenylethanol; buffer components such as sodium chloride, sodium borate, sodium acetate; buffer substances of gluconic acid type; sorbitan monolaurate; triethanolamine; polyoxyethylenesorbitan monopalmitate; dioctylsodium sulfosuccinate; monothioglycerol; thiosorbitol; ethylenediamine tetraacetate.

Suitable vehicles for ophthalmological use can be employed as a solid or non-solid carrier substance for the present invention: As the carriers, there may be mentioned: standard phosphate buffer vehicles (e.g. sodium phosphate buffers, and potassium phosphate buffers); isotonic borate vehicles; isotonic sodium chloride vehicles; and isotonic sodium borate vehicles.

The drug preparation may be used in the form of solid inserts which can remain in a nearly perfect form after administration, or of bio-degradable inserts which can dissolve in tear fluid or disintegrate by any other mechanism.

In general, the active ingredient of the present invention can be used at a dose of from the lowest limit of about 0.001 mg, preferably from about 0.01 mg, to the highest limit of about 50 mg, preferably to about 20 mg, per kg. Depending upon the daily dosage required, administration may be carried out by single dose or divided doses. Unit administration may be also possible.

THE BEST MODE FOR CARRING OUT THE INVENTION

Preparation examples and Reference examples shown below will explain the present invention more concretely.

PREPARATION EXAMPLE 1

Eye Drop Preparation

| | |
|---|---|
| Active ingredient | 0.002 g |
| Dibasic sodium phosphate | 0.716 g |
| Monobasic sodium phosphate | 0.728 g |
| Sodium chloride | 0.400 g |
| Methyl p-hydroxybenzoate | 0.026 g |
| Propyl p-hydroxybenzoate | 0.014 g |
| Sterilized purified water | Suitable amount |
| Sodium hydroxide | Suitable amount |
| Total | 100 ml |

After adjustment to pH 7.0, an eye drop liquid was prepared by conventional means.

PREPARATION EXAMPLE 2

Eye Drop Preparation

| | |
|---|---|
| Active ingredient | 0.002 g |
| Dibasic sodium phosphate | 0.500 g |
| Monobasic sodium phosphate | 1.100 g |
| Sodium chloride | 0.300 g |
| Benzethonium chloride | 0.010 g |
| Sterilized purified water | Suitable amount |
| Total | 100 ml |

After adjustment to pH 7.0, an eye drop liquid was prepared by conventional means.

PREPARATION EXAMPLE 3

Eye Drop Preparation

| | |
|---|---|
| Active ingredient | 0.002 g |
| Dibasic sodium phosphate | 0.400 g |
| Monobasic sodium phosphate | 1.000 g |
| Sodium chloride | 0.690 g |
| 10% Benzalkonium chloride solution | 100 µl |
| Sterilized purified water | Suitable amount |
| Total | 100 ml |

After adjustment to pH 7.0, an eye drop liquid was prepared by conventional means.

REFERENCE EXAMPLE 1

4-(1-Hydroxy-1-methyethyl)-2-propyl-1-[4-(2-tetrazol-5-yl)benzyl]imidazole-5-carboxylic acid To 10 ml N,N-dimethylacetamide solution containing 1.00 g of ethyl 5-(1-hydroxy-1-methylethyl)-2-propylimidazole-4-carboxylate, 0.20 g of 55% sodium hydride in oil was added.

After stirring the reaction mixture for 30 minutes at room temperature, 20 ml N,N-dimethylacetamide solution containing 1.95 g of 4-(2-trityltetrazol-5-yl)benzyl bromide was added dropwise to the reaction mixture.

The reaction mixture was stirred for 2 hours at room temperature, then ethyl acetate and water were added to it and the ethyl acetate layer separated. The extracted solution was washed with water, dried over anhydrous magnesium sulfate and the solvent was distilled off under a reduced pressure. The residue was subjected to silica gel column chromatography in which the solvent system was hexane-ethyl acetate (1:1) to obtain 1.51 g of crystalline ethyl 4-(1-hydroxy-1-methylethyl)-2-propyl-1-[4-(2-trityltetrazol-5-yl)benzyl]imidazole-5-carboxylate.

m.p.: 187–189° C. NMR spectrum (CDCl$_3$) ppm: 0.98 (3H, t, J=7.5 Hz), 1.20 (3H, t, J=7.5 Hz), 1.68 (6H, s), 1.65–1.78 (2H, m), 2.66 (2H, t, J=8 Hz), 4.24 (2H, q, J=7.5 Hz), 5.53 (2H, s), 5.78 (1H, s), 7.04 (2H, d, J=8Hz), 7.17–7.41 (15H, m), 8.13 (2H, d, J=8 Hz)

In a mixed solution of 15 ml of acetic acid with 5 ml of water, 1.40 g of the compound obtained above was dissolved. The solution was stirred for 3.5 hours at 60° C., then cooled, and the precipitate was filtered off. A small amount of the remaining acetic acid and water were distilled off by azeotropy with toluene. The residue was subjected to silica gel column chromatography in which the solvent system was methanol-methylene chloride (1:4) to obtain 0.78 g of gummy ethyl 4-(1-hydroxy-1-methylethyl)-2-propyl-1-[4-(2-tetrazol-5-yl)benzyl]imidazole-5-carboxylate.

In 12 ml of dioxane solution containing 0.78 g of the said compound, 11 ml of water containing 0.486 g of lithium hydroxide monohydrate was added, and stirred at room temperature for 4.5 hours. Dioxane was distilled off under a reduced pressure. To the remaining water solution, 11.6 ml of 1N hydrochloric acid was added. Sodium chloride was further added to it to salt out. The target compound was extracted with ethyl acetate. The extracted solution was dried over anhydrous magnesium sulfate and the solvent was distilled off under a reduced pressure to obtain a crystalline residue. After filtering with isopropyl ether, 0.41 g of the target compound was obtained.

m.p.: 194–196° C. NMR spectrum (DMSO-d$_6$) ppm: 0.89 (3H, t, J=7.5 Hz), 1.58 (6H, s), 1.62 (2H, sextet, J=7.5 Hz), 2.63 (2H, t, J=8 Hz), 5.71 (2H, s), 7.18 (2H, d, J=8.5 Hz), 8.00 (2H, d, J=8.5 Hz)

We claim:

1. A method of treating ocular hypertension and/or glaucoma comprising administering a composition suitable for local application to the eyes of a mammal having ocular hypertension and/or glaucoma, said composition comprising an effective amount of a compound having a formula (I):

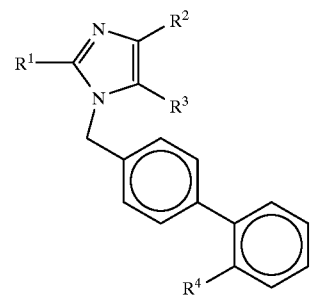

wherein $R^1$ represents a lower alkyl group, a lower alkenyl group or a group of a formula: $R^5$—A—B— wherein $R^5$ represents a hydrogen atom, a lower alkyl group, a cycloalkyl group or an aliphatic acyl group; A represents an oxygen atom or a sulfur atom; and B represents a single bond or a lower alkylene group $R^2$ represents a lower alkyl group, a lower alkenyl group or a group of a formula: —C($R^6$)($R^7$)($R^8$) wherein $R^6$ represents a hydroxyl group or a lower alkoxy group; and $R^7$ and $R^8$ are the same or different and each represents a hydrogen atom, a lower alkyl group, a lower alkenyl group, a lower alkynyl group, a cycloalkyl group, an aryl group or an aralkyl group;

$R^3$ represents a carboxyl group or a group of a formula: —$CON(R^9)(R^{10})$ wherein $R^9$ and $R^{10}$ are the same or different and each represents a hydrogen atom, a lower alkyl group or a lower alkyl group substituted by 1 to 3 substituents selected from substituent group (I);

substituent group (I): an aryl group, a 5- or 6-membered heteroaromatic ring group, a halogen atom, a hydroxyl group, a lower alkoxy group, a carboxyl group, a lower alkoxycarbonyl group, an amino group, an aliphatic acylamide group and an aromatic acylamide group; and $R^4$ represents a carboxyl group, a carboxycarbonyl group or tetrazol-5-yl group;

or a pharmacologically acceptable salt or ester thereof.

2. The method of claim 1, wherein $R^1$ represents a lower alkyl group or a lower alkenyl group.

3. The method of claim 1, wherein $R^1$ represents a lower alkyl group.

4. The method of claim 1, wherein $R^1$ represents an alkyl group containing 2 to 4 carbon atoms.

5. The method of claim 1, wherein $R^2$ represents a group of a formula: —$C(R^6)(R^7)(R^8)$ wherein $R^6$ represents a hydroxyl group or a lower alkoxy group; and $R^7$ and $R^8$ are the same or different and each represents a hydrogen atom or a lower alkyl group.

6. The method of claim 1, wherein $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 to 4 carbon atoms.

7. The method of claim 1, wherein $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 or 2 carbon atoms.

8. The method of claim 1, wherein $R^3$ represents a carboxyl group or a group of a formula:
—$CON(R^9)(R^{10})$ wherein $R^9$ and $R^{10}$ are the same or different and each represents a hydrogen atom or a lower alkyl group.

9. The method of claim 1, wherein $R^3$ represents a carboxyl group.

10. The method of claim 1, wherein $R^4$ represents a carboxyl group or a tetrazol-5-yl group.

11. The method of claim 1, wherein $R^4$ represents a tetrazol-5-yl group.

12. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group or a lower alkoxy group, and $R^7$ and $R^8$ are the same or different and each represents a hydrogen atom or a lower alkyl group; $R^3$ represents a carboxyl group or a group of a formula: —$CON(R^9)(R^{10})$ wherein $R^9$ and $R^{10}$ are the same or different and each represents a hydrogen atom or a lower alkyl group; and $R^4$ represents a carboxyl group or a tetrazol-5-yl group.

13. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group or a lower alkoxy group, and $R^7$ and $R^8$ are the same or different and each represents a hydrogen atom or a lower alkyl group; $R^3$ represents a carboxyl group or a group of a formula: —$CON(R^9)(R^{10})$ wherein $R^9$ and $R^{10}$ are the same or different and each represents a hydrogen atom or a lower alkyl group; and $R^4$ represents a tetrazol-5-yl group.

14. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group or a lower alkoxy group, and $R^7$ and $R^8$ are the same or different and each represents a hydrogen atom or a lower alkyl group; $R^3$ represents a carboxyl group; and $R^4$ represents a carboxyl group or a tetrazol-5-yl group.

15. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group or a lower alkoxyl group, and $R^7$ and $R^8$ are the same or different and each represents a hydrogen atom or a lower alkyl group; $R^3$ represents a carboxyl group; and $R^4$ represents a tetrazol-5-yl group.

16. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 to 4 carbon atoms; $R^3$ represents a carboxyl group or a group of a formula: —$CON(R^9)(R^{10})$ wherein $R^9$ and $R^{10}$ are the same or different and each represents a hydrogen atom or a lower alkyl group; and $R^4$ represents a carboxyl group or a tetrazol-5-yl group.

17. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 to 4 carbon atoms; $R^3$ represents a carboxyl group or a group of a formula: —$CON(R^9)(R^{10})$ wherein $R^9$ and $R^{10}$ are the same or different and each represents a hydrogen atom or a lower alkyl group; and $R^4$ represents a tetrazol-5-yl group.

18. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 to 4 carbon atoms; $R^3$ represents a carboxyl group; and $R^4$ represents a carboxyl group or a tetrazol-5-yl group.

19. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 to 4 carbon atoms; $R^3$ represents a carboxyl group; and $R^4$ represents a tetrazol-5-yl group.

20. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 or 2 carbon atoms; $R^3$ represents a carboxyl group or a group of formula: —$CON(R^9)(R^{10})$ wherein $R^9$ and $R^{10}$ are the same or different and each represents a hydrogen atom or a lower alkyl group; and $R^4$ represents a carboxyl group or a tetrazol-5-yl group.

21. The method of claim 1, wherein: $R^1$ represents a lower alkyl group or a lower alkenyl group; $R^2$ represents a group of a formula: —$C(R^6)(R^7)(R^8)$ wherein $R^6$ represents a hydroxyl group, and $R^7$ and $R^8$ are the same or different and each represents a hydrogen atom or an alkyl group containing 1 or 2 carbon atoms; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a tetrazol-5-yl group.

22. The method of claim 1, wherein: $R^1$ represents a lower alkyl group or a lower alkenyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group; and $R^4$ represents a carboxyl group or a tetrazol-5-yl group.

23. The method of claim 1, wherein: $R^1$ represents a lower alkyl group or a lower alkenyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group; and $R^4$ represents a tetrazol-5-yl group.

24. The method of claim 1, wherein: $R^1$ represents a lower alkyl group; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a carboxyl group or a tetrazol-5-yl group.

25. The method of claim 1, wherein: $R^1$ represents a lower alkyl group; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a tetrazol-5-yl group.

26. The method of claim 1, wherein: $R^1$ represents a lower alkyl group; $R^2$ represents a group of a formula: —C($R^6$)($R^7$)($R^8$) wherein $R^6$ represents a hydroxyl or lower alkoxy group, and $R^7$ and $R^8$ are the same or different and each represents a hydrogen atom or a lower alkyl group; $R^3$ represents a carboxyl group; and $R^4$ represents a carboxyl group or a tetrazol-5-yl group.

27. The method of claim 1, wherein $R^1$ represents a lower alkyl group; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group; and $R^4$ represents a tetrazol-5-yl group.

28. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group or a group of a formula:
—CON($R^9$)($R^{10}$) wherein $R^9$ and $R^{10}$ are the same or different and each represents a hydrogen atom or a lower alkyl group; and $R^4$ represents a carboxyl group or a tetrazol-5-yl group.

29. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group or a group of a formula:
—CON($R^9$)($R^{10}$) wherein $R^9$ and $R^{10}$ are the same or different and each represents a hydrogen atom or a lower alkyl group; and $R^4$ represents a tetrazol-5-yl group.

30. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group; and $R^4$ represents a carboxyl group or a tetrazol-5-yl group.

31. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group; and $R^4$ represents a tetrazol-5-yl group.

32. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group or a group of a formula:
—CON($R^9$)($R^{10}$) wherein $R^9$ and $R^{10}$ are the same or different and each represents a hydrogen atom or a lower alkyl group; and $R^4$ represents a carboxyl group or a tetrazol-5-yl group.

33. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group or a group of a formula:
—CON ($R^9$)($R^{10}$) wherein $R^9$ and $R^{10}$ are the same or different and each represents a hydrogen atom or a lower alkyl group; and $R^4$ represents a tetrazol-5-yl group.

34. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R_8$ are the same or different and each represents a hydrogen atom or an alkyl group containing 1 or 2 carbon atoms; $R^3$ represents a carboxyl group; and $R^4$ represents a carboxyl group or a tetrazol-5-yl group.

35. The method of claim 1, wherein: $R^1$ represents a lower alkyl group; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group; and $R^4$ represents a tetrazol-5-yl group.

36. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a carboxyl group or a tetrazol-5-yl group.

37. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a tetrazol-5-yl group.

38. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group; and $R^4$ represents a carboxyl group or a tetrazol-5-yl group.

39. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group or a lower alkoxy group, and $R^7$ and $R^8$ are the same or different and each represents a hydrogen atom or a lower alkyl group; $R^3$ represents a carboxyl group; and $R^4$ represents a tetrazol-5-yl group.

40. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms); $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a carboxyl group or a tetrazol-5-yl group.

41. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a tetrazol-5-yl group.

42. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group; and $R^4$ represents a carboxyl group or a tetrazol-5-yl group.

43. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 to 4 carbon atoms; $R^3$ represents a carboxyl group; and $R^4$ represents a tetrazol-5-yl group.

44. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a carboxyl group or a tetrazol-5-yl group.

45. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group or a group of a formula: —CON($R^9$)($R^{10}$) wherein $R^9$ and $R^{10}$ are the same or different and each represents a hydrogen atom or a lower alkyl group; and $R^4$ represents a tetrazol-5-yl group.

46. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group; and $R^4$ represents a carboxyl group or a tetrazol-5-yl group.

47. The method of claim 1, wherein: $R^1$ represents an alkyl group containing 2 to 4 carbon atoms; $R^2$ represents a group of a formula: —C($R^6$)($R^7$)($R^8$) wherein $R^6$ represents a hydroxyl group, and $R^7$ and $R^8$ are the same or different and each represents a hydrogen atom or an alkyl group containing 1 or 2 carbon atoms; $R^3$ represents a carboxyl group; and $R^4$ represents a tetrazol-5-yl group.

48. The method of claim 1, wherein:

$R^1$ represents a lower alkyl group;

$R^2$ represents a lower alkyl group or a group of formula —C($R^6$)($R^7$)($R^8$) wherein $R^6$ represents a hydroxyl group and $R^7$ and $R^8$ are the same or different and each represents a hydrogen atom or a lower alkyl group;

$R^3$ represents a carboxy group; and $R^4$ represents a carboxy group, a carboxycarbonyl group or a tetrazol-5-yl group;

or a pharmacologically acceptable salt or ester thereof.

49. The method of claim 1, wherein:

$R^1$ represents an alkyl group having from 2 to 4 carbon atoms;

$R^2$ represents a lower alkyl group or a group of formula —C($R^6$)($R^7$)($R^8$) wherein $R^6$ represents a hydroxyl group and $R^7$ and $R^8$ are the same or different and each represents a hydrogen atom or a lower alkyl group;

$R^3$ represents a carboxy group; and $R^4$ represents a carboxy group, a carboxycarbonyl group or a tetrazol-5-yl group;

or a pharmacologically acceptable salt or ester thereof.

50. The method of claim 1, wherein:

$R^1$ represents an alkyl group having from 2 to 4 carbon atoms;

$R^2$ represents a group of formula —C($R^6$)($R^7$)($R^8$) wherein $R^6$ represents a hydroxyl group, and $R^7$ and $R^8$ are the same or different and each represents a hydrogen atom or a lower alkyl group;

$R^3$ represents a carboxy group; and $R^4$ represents a carboxy group, a carboxycarbonyl group or a tetrazol-5-yl group;

or a pharmacologically acceptable salt or ester thereof.

51. The method of claim 1, wherein:

$R^1$ represents an alkyl group having from 2 to 4 carbon atoms;

$R^2$ represents a group of formula —C($R^6$)($R^7$)($R^8$) wherein $R^6$ represents a hydroxyl group, and $R^7$ and $R^8$ are the same or different and each represents a hydrogen atom or an alkyl group having from 1 to 4 carbon atoms;

R³ represents a carboxy group; and
R⁴ represents a carboxy group, a carboxycarbonyl group or a tetrazol-5-yl group;
or a pharmacologically acceptable salt or ester thereof.
52. The method of claim 1, wherein:
R¹ represents an alkyl group having from 2 to 4 carbon atoms;
R² represents a group of formula —C(R⁶)(R⁷)(R⁸) wherein R⁶ represents a hydroxyl group, and R⁷ and R⁸ are the same or different and each represents a hydrogen atom or an alkyl group having 1 or 2 carbon atoms;
R³ represents a carboxy group; and
R⁴ represents a carboxy group, a carboxycarbonyl group or a tetrazol-5-yl group;
or a pharmacologically acceptable salt or ester thereof.
53. The method of claim 1, wherein:
R¹ represents an alkyl group having from 2 to 4 carbon atoms;
R² represents a lower alkyl group or a group of formula —C(R⁶)(R⁷)(R⁸) wherein R⁶ represents a hydroxyl group and R⁷ and R⁸ are the same or different and each represents a hydrogen atom or a lower alkyl group;
R³ represents a carboxy group; and
R⁴ represents a carboxy group or a tetrazol-5-yl group;
or a pharmacologically acceptable salt or ester thereof.
54. The method of claim 1, wherein:
R¹ represents an alkyl group having from 2 to 4 carbon atoms;
R² represents a group of formula —C(R⁶)(R⁷)(R⁸) wherein R⁶ represents a hydroxyl group, and R⁷ and R⁸ are the same or different and each represents a hydrogen atom or an alkyl group having from 1 to 4 carbon atoms;
R³ represents a carboxy group; and
R⁴ represents a carboxy group or a tetrazol-5-yl group;
or a pharmacologically acceptable salt or ester thereof.
55. The method of claim 1, wherein:
R¹ represents an alkyl group having from 2 to 4 carbon atoms;
R² represents a group of formula —C(R⁶)(R⁷)(R⁸) wherein R⁶ represents a hydroxyl group, and R⁷ and R⁸ are the same or different and each represents a hydrogen atom or an alkyl group having 1 or 2 carbon atoms;
R³ represents a carboxy group; and
R⁴ represents a carboxy group or a tetrazol-5-yl group;
or a pharmacologically acceptable salt or ester thereof.
56. The method of claim 1, wherein:
R¹ represents an alkyl group having from 2 to 4 carbon atoms;
R² represents a lower alkyl group or a group of formula —C(R⁶)(R⁷)(R⁸) wherein R⁶ represents a hydroxyl group and R⁷ and R⁸ are the same or different and each represents a hydrogen atom or a lower alkyl group;
R³ represents a carboxy group; and
R⁴ represents a tetrazol-5-yl group;
or a pharmacologically acceptable salt or ester thereof.
57. The method of claim 1, wherein:
R¹ represents an alkyl group having from 2 to 4 carbon atoms;
R² represents a group of formula —C(R⁶)(R⁷)(R⁸) wherein R⁶ represents a hydroxyl group, and R⁷ and R⁸ are the same or different and each represents a hydrogen atom or an alkyl group having from 1 to 4 carbon atoms;
R³ represents a carboxy group; and
R⁴ represents a tetrazol-5-yl group;
or a pharmacologically acceptable salt or ester thereof.
58. The method of claim 1, wherein:
R¹ represents an alkyl group having from 2 to 4 carbon atoms;
R² represents a group of formula —C(R⁶)(R⁷)(R⁸) wherein R⁶ represents a hydroxyl group, and R⁷ and R⁸ are the same or different and each represents a hydrogen atom or an alkyl group having 1 or 2 carbon atoms;
R³ represents a carboxy group; and
R⁴ represents a tetrazol-5-yl group;
or a pharmacologically acceptable salt or ester thereof.
59. The method of claim 1, wherein said compound of formula (I) is selected from the group consisting of:

-continued
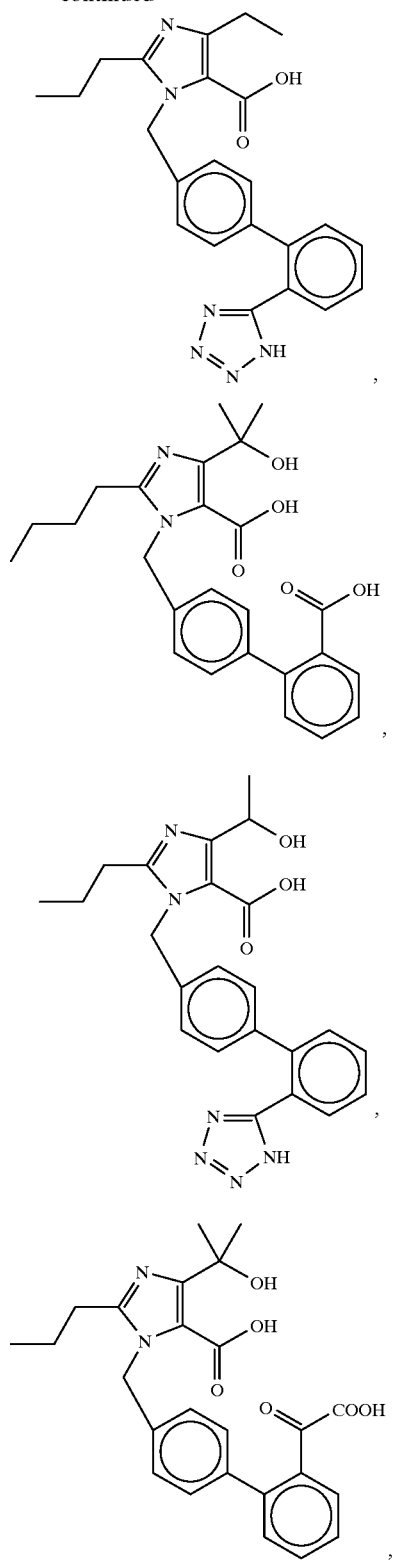
pharmacologically acceptable salts thereof and pharmacologically acceptable esters thereof.
60. The method of claim 1, wherein said compound of formula (I) is selected from the group consisting of:
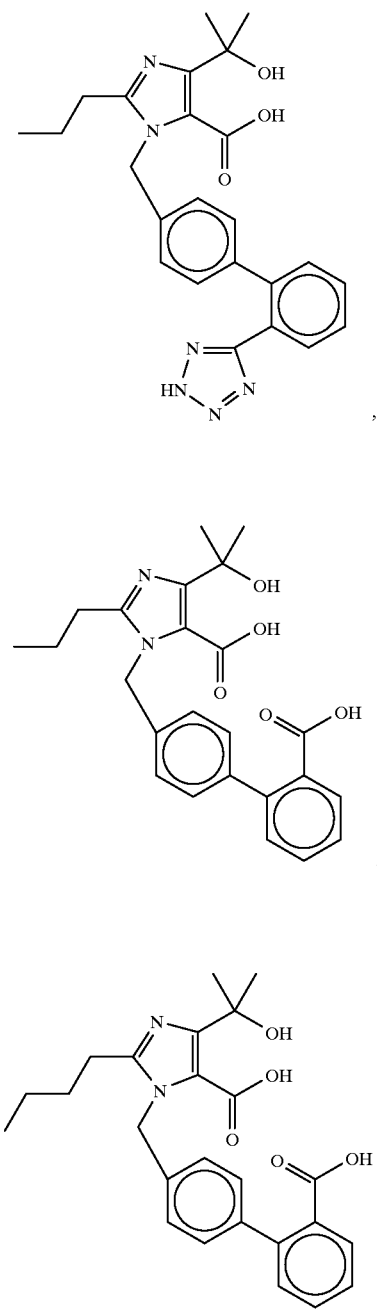

-continued

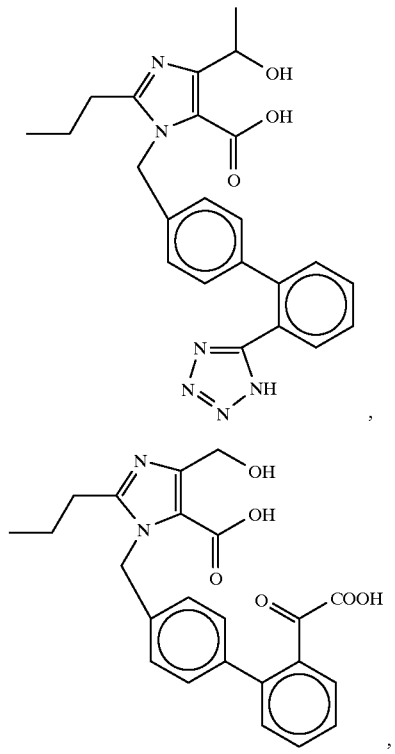

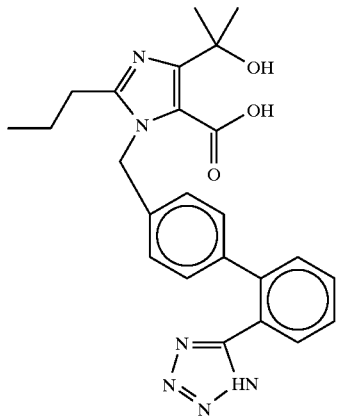

pharmacologically acceptable salts thereof and pharmacologically acceptable esters thereof.

61. The method of claim 1, which comprises administering an effective amount of a compound having a formula:

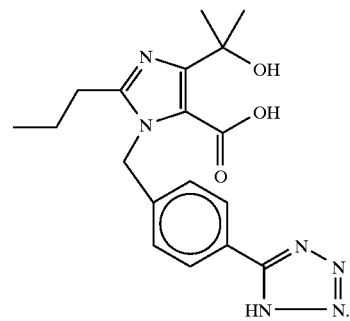

or a pharmacologically acceptable salt or ester thereof.

62. The method of claim 1, wherein said compound of formula (I) is administered as eye drops.

63. A method of treating ocular hypertension and/or glaucoma comprising administering an effective amount of a composition suitable for local application to the eyes of a mammal having ocular hypertension and/or glaucoma, said composition comprising an effective amount of a compound having the following formula:

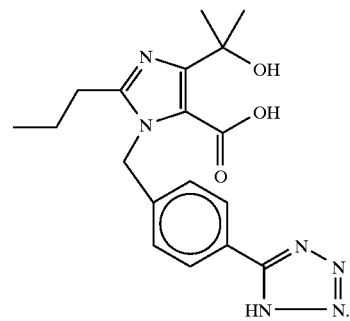

64. A method of treating ocular hypertension and/or glaucoma comprising administering an effective amount of a composition suitable for local application to the eyes of a mammal having ocular hypertension and/or glaucoma, said composition comprising an effective amount of a compound having the following formula:

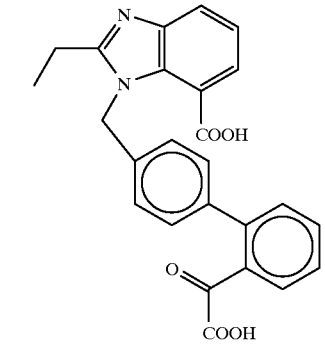

* * * * *

UNITED STATES PATENT AND TRADEMARK OFFICE
CERTIFICATE OF CORRECTION

PATENT NO.   : 5,925,664
DATED        : July 20, 1999
INVENTOR(S)  : Yokoyama et al.

It is certified that error appears in the above-identified patent and that said Letters Patent is hereby corrected as shown below:

Title page,
Left column, Item [30], under "Foreign Application Priority Data", delete "Mar. 16, 1995 [JP] Japan ...... 5-000444".

Column 3,
Line 17, after "(6)", delete "$R^1$" and insert -- $R^2$ --.

Column 4,
Line 50, delete "$R^1$" and insert -- $R^{10}$ --.

Column 5,
Line 21, "-C($R^9$) ($R^7$) ($R^8$)" and insert -- -C ($R^6$) ($R^7$) ($R^8$) --.

Column 25,
Delete lines 1-10.

Column 26,
Delete lines 1-10.

Column 27,
Delete lines 1-8.

Signed and Sealed this

Twentieth Day of November, 2001

Attest:

*Nicholas P. Godici*

NICHOLAS P. GODICI
*Attesting Officer*    *Acting Director of the United States Patent and Trademark Office*